(12) United States Patent
Assenheimer

(10) Patent No.: US 6,993,383 B2
(45) Date of Patent: Jan. 31, 2006

(54) ANOMALY DETECTION BASED ON SIGNAL VARIATIONS

(75) Inventor: Michel Assenheimer, Kfar-Saba (IL)

(73) Assignee: Mirabel Medical Systems Ltd., Migdal-Haemek (IL)

( * ) Notice: Subject to any disclaimer, the term of this patent is extended or adjusted under 35 U.S.C. 154(b) by 227 days.

(21) Appl. No.: 10/155,888

(22) Filed: May 23, 2002

(65) Prior Publication Data

US 2003/0004432 A1 Jan. 2, 2003

(30) Foreign Application Priority Data

May 24, 2001 (IL) .................................. 143374

(51) Int. Cl.
*A61B 5/05* (2006.01)

(52) U.S. Cl. .................................................. 600/547
(58) Field of Classification Search ................ 600/547, 600/372, 382, 384, 386, 461, 476, 477, 478, 600/552–555
See application file for complete search history.

(56) References Cited

U.S. PATENT DOCUMENTS

| | | |
|---|---|---|
| 4,291,708 A | 9/1981 | Frei et al. |
| 4,458,694 A | 7/1984 | Sollish et al. |
| 4,537,203 A | 8/1985 | Machida |
| 5,311,878 A | 5/1994 | Brown et al. |
| 5,441,051 A * | 8/1995 | Hileman et al. ............ 600/454 |
| 5,615,672 A | 4/1997 | Braig et al. |
| 5,651,955 A | 7/1997 | Klaveness |
| 5,733,525 A | 3/1998 | Klaveness |
| 5,746,214 A | 5/1998 | Brown et al. |
| 5,810,010 A | 9/1998 | Anbar |
| 5,810,742 A | 9/1998 | Pearlman |
| 5,947,910 A * | 9/1999 | Zimmet ....................... 600/547 |
| 5,987,346 A | 11/1999 | Benaron et al. |
| 6,109,270 A | 8/2000 | Mah et al. |
| 6,385,474 B1 * | 5/2002 | Rather et al. ............... 600/407 |
| 6,416,740 B1 | 7/2002 | Unger |
| 6,558,665 B1 | 5/2003 | Cohen et al. |
| 6,797,257 B2 | 9/2004 | McDonald et al. |
| 2001/0051774 A1 * | 12/2001 | Littrup et al. ............... 600/547 |
| 2003/0138378 A1 | 7/2003 | Hashimshony |

FOREIGN PATENT DOCUMENTS

| | | |
|---|---|---|
| GB | 2 138 148 | 10/1984 |
| WO | WO 01/89379 | 11/2001 |

OTHER PUBLICATIONS

Piperno, G. et al.; "Breast Cancer Screening by Impedance Measurements;" 1990; Frontiers Med. Biol. Eng.; vol. 2; pp. 111–117.

Eyuboglu, Murat, B. et al.; "In Vivo Imaging of Cardiac Related Impedance Changes;" Mar. 1989; IEEE Engineering in Medicine and Biology Magazine; No. 1; pp. 39–45.

Record, P. M. et al.; "Multifrequency Electrical Impedance Tomography;" 1992; Clinical Physics and Physiological Measurement; vol. 13; Supplement A; pp. 67–72.

Riu, P. et al.; "In Vivo Static Imaging for the Real and Reactive Parts in Electrical Impedance Tomography Using Multifrequency Techniques;" Oct. 29, 1992; IEEE Proceedings of the Annual International Conference of the Engineering in Medicine and Biology Society; vol. 5; No. 14; pp. 1706–1707; XP000514393.

* cited by examiner

*Primary Examiner*—Eric F. Winakur
*Assistant Examiner*—Matthew Kremer
(74) *Attorney, Agent, or Firm*—Fenster & Company

(57) ABSTRACT

A method of analyzing the type of tissue of a body portion of a subject. The method includes applying an excitation signal to the subject, sensing electrical signals from the subject responsive to the excitation signal, determining a stationary impedance map of the body portion responsive to the sensed signals, determining a change waveform of at least a part of the stationary impedance map, and providing an indication on a tissue type of at least part of the body portion, responsive to the change waveform.

35 Claims, 5 Drawing Sheets

ANOMALY DETECTION BASED ON SIGNAL VARIATIONS

FIELD OF THE INVENTION

The present invention relates to systems for tissue characterization.

BACKGROUND OF THE INVENTION

Variations in electrical impedance of the human tissue may be indicative of tumors, lesions and other anomalies. For example, U.S. Pat. No. 4,291,708 to Frei, and U.S. Pat. No. 4,458,694, and the article, "Breast Cancer Screening by Impedance Measurements," by G. Pipemo et al., Frontiers Med. Biol. Eng., Vol. 2 pp. 111–117, the disclosures of which are incorporated herein by reference, describe systems for determining the impedance between a point on the surface of the skin and some reference point on the body of the patient. With the use of a multi-element probe, a two-dimensional impedance map of an organ such as a breast can be generated. The impedance map, describing variations in impedance along the tissue of the organ, can be used for the detection of tumors and especially malignant tumors.

One of the factors which influences the chances of curing a patient having a malignant tumor is early detection of the tumor. Therefore, although many tumors are detectable using prior art impedance imaging systems, it is continuously desired to improve the resolution of these systems to allow earlier detection of anomalies which may be malignant tumors.

U.S. Pat. No. 4,291,708 to Frei, mentioned above, and U.S. Pat. No. 5,810,742 to Pearlman the disclosure of which is incorporated herein by reference, describe methods of impedance imaging of an organ. A multi-element probe is placed on a surface of the organ and a reference signal is applied to the human body including the organ at a reference point far from the imaged organ. The resolution of the system depends on the resolution of a sensor of the probe and/or on the signal strength of the reference signal. When a digital sensor is used, increasing the resolution may be achieved by performing analog to digital conversion over the entire dynamic range. This, however, increases the cost and power consumption of the probe. Increasing the signal strength of the reference signal is not desirable for reasons of safety, patient discomfort and power consumption.

The blood volume of organs of the human body changes with the cardiac cycle (heart cycle) of the human. The detection of the changes in the blood volume is referred to as plethysmography. Plethysmography is commonly used to determine the phase of the cardiac cycle, as described in U.S. Pat. No. 5,615,672, the disclosure of which is incorporated herein by reference, and in pulse oximeters which measure blood oxygen saturation.

UK patent application GB 2,138,148, the disclosure of which is incorporated herein by reference, states that impedance changes which are correlated with the cardiac, respiratory or other functions of the body, may be recorded, for example, for an evaluation of the stroke-volume of the heart and respiration and perfusion of the lungs. An article titled "In Vivo Imaging of Cardiac Related Impedance Changes", B. Murat et al., the disclosure of which is incorporated herein by reference, states that it has been shown that the thoracic resistance variations during the cardiac cycle can be imaged by ECG-gated electrical impedance tomography (EIT). This article describes using EIT to image the blood flow to the lungs to detect abnormalities in pulmonary perfusion, such as pulmonary embolism.

U.S. Pat. No. 5,810,010 to Anbar, the disclosure of which is incorporated herein by reference, describes a method of cancer detection based on temporal periodic changes. The temporal periodic changes are suggested to be detected based on dynamic area thermometry (DAT), infrared sensing, MRI, or ultrasound.

Web pages available on May, 1, 2001 at www.dobimedical.com, the disclosure of which is incorporated herein by reference, describes a breast cancer detection system which measures transmission of red light through the breast. The system records the transient response to a pressure stimulus that initiates changes in blood volume and hemoglobin oxygenation.

SUMMARY OF THE INVENTION

An aspect of some embodiments of the present invention relates to detecting, locating and/or analyzing anomalies based on impedance signals which are indicative of changes in the blood volume and/or of the blood flow through an examined body region of a subject. In some embodiments of the invention, the amplitude of the change in the blood volume signals and/or the amplitude of the blood flow signals are used to aid in anomaly detection, location and/or analysis. Anomalies generally have different blood volume than normal tissue. Therefore, the amplitude of signals representing the blood volume, the blood flow and/or the changes in the blood volume and/or blood flow through an examined region are indicative of whether an anomaly is located within the examined region, the depth of the anomaly within the region and/or the type of the anomaly.

An aspect of some embodiments of the present invention relates to detecting, locating and/or analyzing anomalies in a patient, based on a signal which corresponds to and/or is gated by a related event in the patient. In some embodiments of the invention, the signal which corresponds to and/or is gated by a related event is extracted from signals sensed from the body region. Thus, the signal used an analyzing the anomaly is closely related to the related event and does not generally include high levels of unrelated noise.

In some embodiments of the invention, the related event comprises a cyclic body variation such as the cardiac cycle and/or pulmonary cycle of the subject. Alternatively or additionally, the related event comprises an internal non-cyclic variation, such as the heart beats of a subject with a non-regular cardiac cycle.

In some embodiments of the invention, the related event comprises an external stimuli, such as injection of a stimulation material and/or application of pressure to the body region. In some embodiments of the invention, signals indicative of changes in the blood flow and/or blood volume are extracted for different stimuli levels and/or for different events. A comparison of one or more parameters for the different stimuli levels and/or for different events is used to determine the type of the tissue in the examined region.

Optionally, the type of the tissue is determined based on the amplitude of the extracted signal. Alternatively or additionally, the type of the tissue is determined based on the time delay between a related event and the effect of the related event on a specific tissue region.

In some embodiments of the invention, the sensed signals are generated by one or more applied signals, for example electrical signals (DC or AC) or light signals, applied to the examined region. Alternatively, the applied signals are applied at a body region of the subject far from the examined body region.

An aspect of some embodiments of the present invention relates to using synchronous detection methods in determining a slowly changing signal carried by a large stationary signal. In some embodiments of the invention, the slowly changing signal has an amplitude at least 10, 50 times smaller than the amplitude of the stationary signal. In some embodiments of the invention, the slowly changing signal is acquired in non-invasive detection of physiological signals from a subject. In an exemplary embodiment of the present invention, the slowly changing signal depends on the blood rate change of the subject. In other embodiments, the slowly changing signal comprises, for example, blood volume, blood pressure, body surface temperature, blood oxygen saturation or blood content level of glucose, alcohol, cholesterol and/or other materials.

An aspect of some embodiments of the present invention relates to determining the cardiac cycle of a subject, based on variations in temperature measurements from the subject. In some embodiments of the invention, the cardiac cycle is determined from variations in surface temperature measurements of the subject.

There is therefore provided in accordance with an embodiment of the present invention, a method of analyzing the type of tissue of a body portion of a subject, comprising applying an excitation signal to the subject, sensing electrical signals from the subject responsive to the excitation signal, determining a stationary impedance map of the body portion responsive to the sensed signals, determining a change waveform of at least a part of the stationary impedance map; and providing an indication on a tissue type of at least part of the body portion, responsive to the change waveform.

Optionally, the method includes generating a change map of a parameter of the change waveform for the at least part of the stationary map. Optionally, generating the change map of a parameter of the change waveform comprises generating a change map of the amplitude of the change waveform. Optionally, the method includes displaying the change map. Optionally, the method includes correlating the change map and the stationary map, for example, displaying the change map overlaid on the stationary map. Optionally, the method includes determining areas of increased perfusion of blood in the body portion, responsive to the change map. Optionally, sensing the signals comprises sensing electrical currents and/or voltages.

Optionally, applying signals to the subject comprises applying electrification signals from at least two electrodes which are electrified with signals of different phases. Optionally, determining the change waveform comprises determining a waveform portion which corresponds to a related event in the patient. Optionally, determining a waveform portion which corresponds to a related event in the patient comprises determining a waveform which is at least partially due to application of an external stimuli to the subject. Optionally, the application of the external stimuli to the subject comprises injecting a stimuli to the blood stream of the subject and/or applying pressure to the body portion of the subject.

Optionally, determining the change waveform comprises determining a waveform which is mostly due to a cyclic variation in the subject. Optionally, the method includes measuring the frequency of the cyclic variation of the subject and wherein determining the change waveform comprises extracting a signal with the measured frequency. Optionally, measuring the frequency of the cyclic variation comprises measuring from the sensed signals.

Optionally, measuring the frequency of the cyclic variation comprises measuring at a different body portion than for which the impedance map is determined. Optionally, determining the waveform comprises determining a waveform which is mostly due to a cardiac cycle or a pulmonary cycle of the subject. Optionally, sensing the signals comprises sensing a plurality of times over a period including a plurality of cycles of the cyclic variation.

Optionally, determining the change waveform comprises determining a waveform which appears a predetermined time after the related event. Optionally, the related event comprises a heart beat of the patient. Optionally, determining the change waveform comprises filtering the change waveform so as to remove frequencies which are due to motion artifacts. Optionally, determining the change waveform comprises removing frequencies above 4 Hz from the change waveform. Optionally, the method includes determining the amplitude of the change waveform. Optionally, sensing the signals comprises sensing from a plurality of points on the surface of the body portion and determining the change waveform for each of the plurality of points.

Optionally, providing the indication on tissue type of at least part of the body portion comprises providing indication on whether an anomaly is located in the body portion, on a type of an anomaly in the body portion and/or on whether the anomaly is malignant.

There is further provided in accordance with an embodiment of the present invention, a method of analyzing the type of tissue of a body portion of a subject, comprising applying an excitation signal to the subject, sensing signals from the subject responsive to the excitation signal, extracting from the sensed signals a time dependent change waveform, filtering the change waveform so at to remove at least one frequency from the change waveform, and providing an indication on a tissue type of at least part of the body portion, responsive to the filtered change waveform.

Optionally, filtering the change waveform comprises filtering so as to remove frequencies which are not due to a cyclic variation in the subject. Optionally, the method includes measuring the frequency of the cyclic variation of the subject and wherein filtering the change waveform comprises extracting a signal with the measured frequency.

Optionally, measuring the frequency of the cyclic variation comprises measuring from the sensed signals. Optionally, measuring the frequency of the cyclic variation comprises measuring at a different body portion than for which the impedance map is determined. Optionally, the cyclic variation comprises a cardiac or pulmonary cycle of the subject.

Optionally, sensing the signals comprises sensing a plurality of times over a period including a plurality of cycles of the cyclic variation. Optionally, filtering the change waveform comprises filtering the change waveform so as to remove frequencies which are due to motion artifacts. Optionally, filtering the change waveform comprises removing frequencies above 4 Hz from the change waveform. Optionally, sensing the signals comprises sensing light signals. Optionally, sensing the light signals comprises sensing infrared signals.

Optionally, sensing the signals comprises sensing electrical signals.

There is further provided in accordance with an embodiment of the present invention, a method of analyzing the type of tissue of a body portion of a subject, comprising applying an excitation signal to the subject, sensing signals from the subject responsive to the excitation signal, determining at least one parameter of an internal event in the subject, extracting from the sensed signals a time dependent change waveform responsive to the at least one parameter of the internal event, and providing an indication on a tissue type of at least part of the body portion, responsive to the change waveform.

Optionally, extracting the change waveform comprises extracting a waveform which appears a predetermined time after the internal event. Optionally, the internal event comprises a heart beat of the patient. Optionally, the internal event comprises a cyclic event and wherein extracting the change waveform comprises extracting a waveform which has a frequency substantially equal to the frequency of the internal event.

There is further provided in accordance with an embodiment of the present invention, a method of analyzing the type of tissue of a body portion of a subject, comprising applying an excitation signal to the subject, sensing signals from the subject responsive to the excitation signal, injecting a stimuli to the blood stream of the subject, extracting from the sensed signals a time dependent change waveform responsive to the injected stimuli, and providing an indication on a tissue type of at least part of the body portion, responsive to the change waveform.

Optionally, the method includes determining the amplitude of the change waveform.

Optionally, sensing the signals comprises sensing from a plurality of points on the surface of the body portion and determining the change waveform for each of the plurality of points. Optionally, providing the indication on tissue type of at least part of the body portion comprises providing indication on whether an anomaly is malignant.

There is further provided in accordance with an embodiment of the present invention, a method of impedance imaging of a body portion of a subject, comprising determining an impedance map of the body portion responsive to the sensed signals, determining a change waveform, related to an event in the subject, of at least a portion of the impedance map, generating a change map of at least one parameter of the change waveform of the at least a portion of the impedance map, and detecting anomalies of suspicious characteristics based on the impedance map and the change map.

Optionally, the event in the subject comprises the cardiac cycle. Optionally, detecting anomalies of suspicious characteristics comprises detecting anomalies which have blood perfusion rates and impedance values characteristic of cancerous tumors. Optionally, the at least one parameter comprises an amplitude.

There is further provided in accordance with an embodiment of the present invention, a method of displaying impedance images of a body portion of a subject, comprising displaying a stationary impedance map including stationary impedance values of a body portion, and displaying, simultaneously with the stationary map, a change map including values indicative of at least one parameter of the change of impedance values of the body portion.

Optionally, the change map is displayed overlaid on the stationary map.

Optionally, the at least one parameter of the change comprises an amplitude of the change. Optionally, the at least one parameter of the change comprises a dominant frequency of the change. Optionally, the at least one parameter of the change comprises a time delay from occurrence of an event in the subject until a response to the event is detected.

There is further provided in accordance with an embodiment of the present invention, apparatus for impedance imaging, comprising at least one probe which applies excitation signals to a subject, at least one sensor which senses signals generated responsive to the excitation signals, from the subject, a processing unit which determines a map of a body portion of the subject responsive to the sensed signals, and a change waveform of at least a portion of the map, and an output unit which provides an indication on the tissue type of the body portion responsive to the change waveform.

Optionally, the output unit comprises a display for displaying a change map indicative of at least one parameter of the change waveforms of the at least a portion of the impedance map. Optionally, the at least one parameter comprises an amplitude. Optionally, the at least one probe comprises an electrode which electrifies the subject in pulses. Optionally, the apparatus includes a probe which determines a cyclic variation of the subject and wherein the processor uses an output from the probe in determining the change waveform.

BRIEF DESCRIPTION OF THE DRAWINGS

Exemplary non-limiting embodiments of the invention will be described with reference to the following description of the embodiments, in conjunction with the figures. Identical structures, elements or parts which appear in more than one figure are preferably labeled with a same or similar number in all the figures in which they appear, and in which.

DETAILED DESCRIPTION OF EMBODIMENTS

Figure 1:
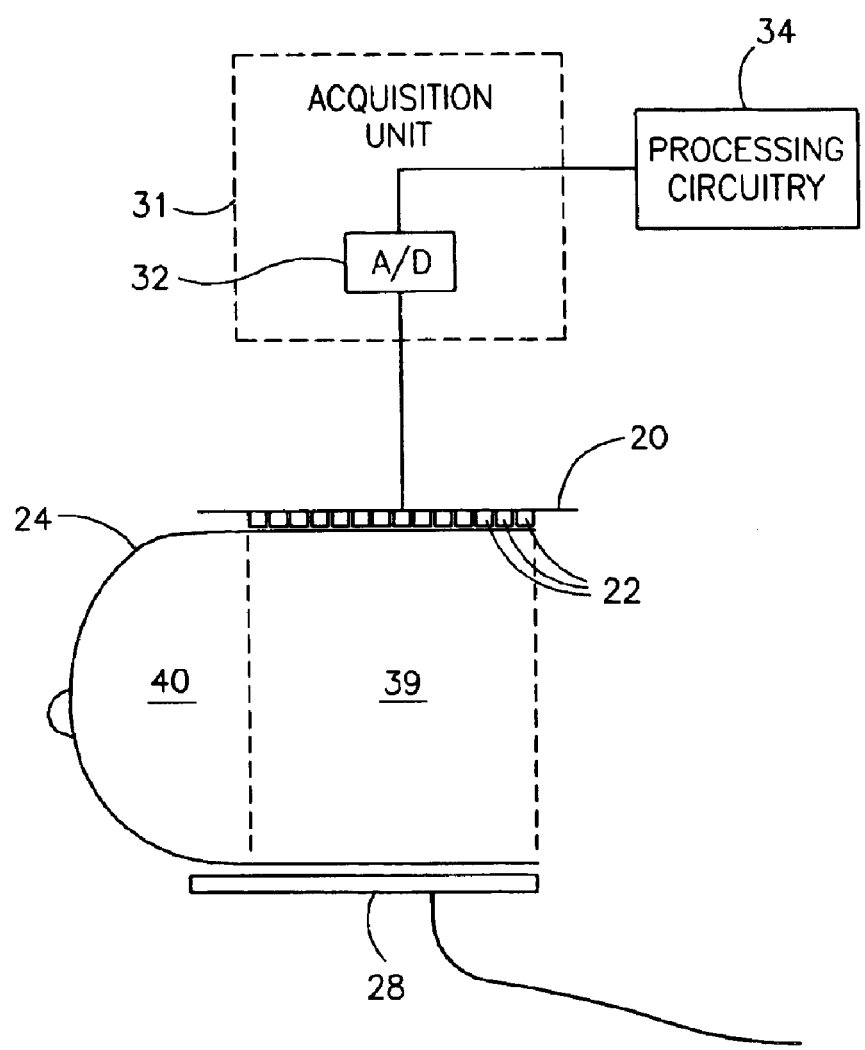
FIG. 1 is a schematic side view of an imaging procedure of a breast, in accordance with an embodiment of the present invention.

FIG. 1 is a schematic side view of an imaging procedure of a breast 40 of a subject, in accordance with an embodiment of the present invention. A probe 20, which includes a plurality of conductive sensing elements 22, is placed against a surface 24 of breast 40. In an embodiment of the invention, an electrode 28 provides electrical excitation to breast 40. For example, electrode 28 is placed against a surface of breast 40 opposite surface 24 on which probe 20 is placed, with a predetermined voltage signal applied thereto. In some embodiments, electrode 28 has substantially the same surface area as probe 20. Probe 20 comprises an acquisition unit 31 which amplifies and digitizes the signals from sensing elements 22 using methods known in the art. In some embodiments of the invention, acquisition unit 31 includes one or more A/D converters 32 which translate the signals sensed by sensing elements 22 to digital samples. Processing circuitry 34, included in probe 20, analyzes the digital samples and forms an impedance map of a region 39 of breast 40 beneath surface 24.

Alternatively to using electrode 28, in some embodiments of the invention, alternative or additional excitation electrodes are used in exciting breast 40. Excitation may be applied from a remote location on the subject, far from breast 40, or from one or more surfaces of breast 40. The excitation may be applied as voltage and/or current signals in one or more frequencies and/or as DC signals.

In some embodiments of the invention, A/D converters 32 comprise high resolution converters, i.e., with a precision of 15 bits or more, in order to allow detection of signals with relatively small amplitudes. Acquisition unit 31 optionally includes low noise amplifiers in order to minimize the noise included in the sensed samples. Alternatively or additionally, the excitation power of the signals applied to electrode 28 is between about 100–500 $\mu A/cm^2$, so as to allow detection of signals with relatively small amplitudes. Alternatively, any other excitation power levels are used, for example lower levels of between about 10–100 $\mu A/cm^2$.

In an exemplary embodiment of the present invention, probe 20 comprises an 8×8 array of sensing elements 22, although any other arrangement and/or number of sensing elements 22 may be used. In some embodiments of the invention, each sensing element 22 has a separate respective A/D, allowing concurrent sensing of signals by all of sensing elements 22. Alternatively, a single A/D converter 32 is used for each group of sensing elements 22 of probe 20, e.g., for each column or row of probe 20 or for all of sensing elements 22 in probe 20. In some embodiments of the invention, each time a sample is to be taken, acquisition unit 31 sweeps through all of sensing elements 22 taking a measurement from each of the sensing elements using the same A/D converter 32.

Figure 2:
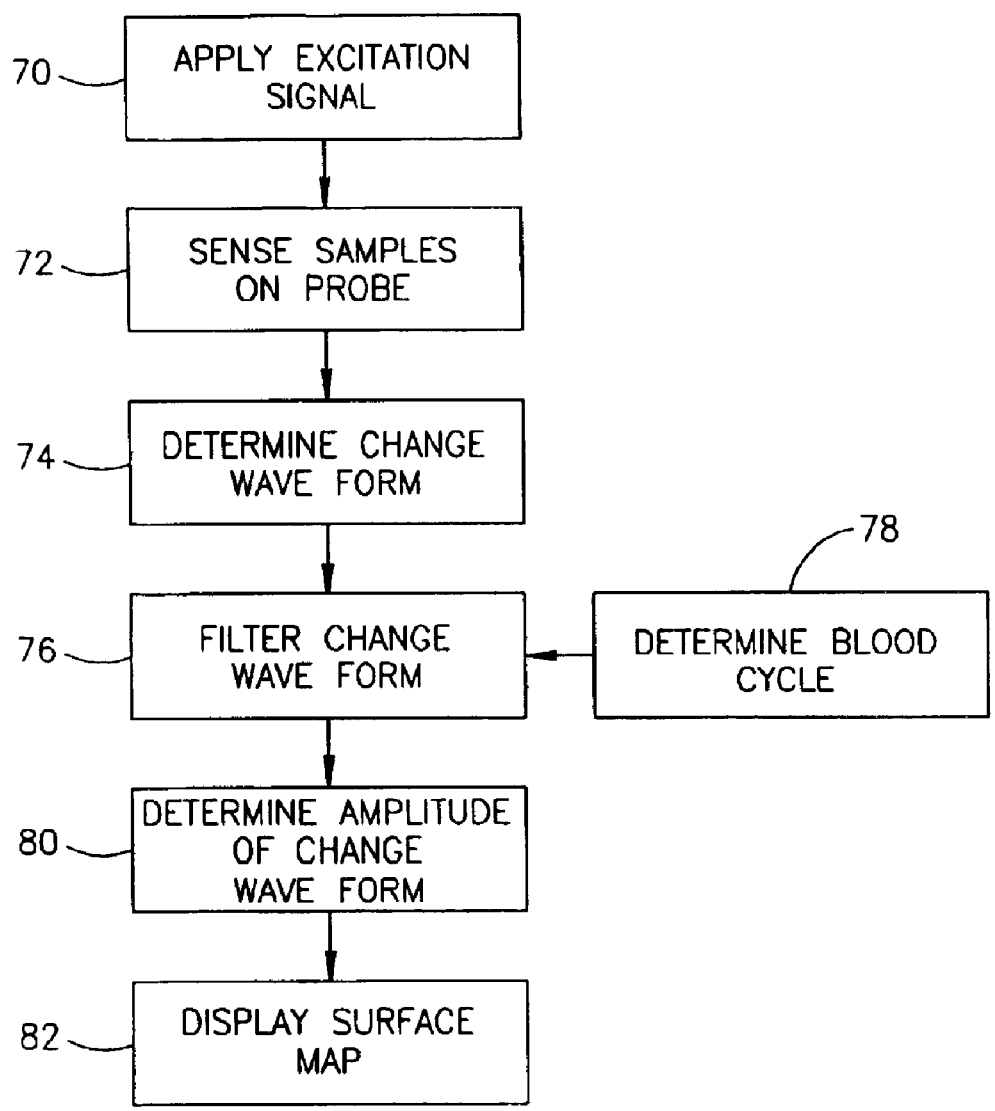
FIG. 2 is as flowchart of the actions performed during an impedance imaging procedure, in accordance with some embodiments of the present invention.

FIG. 2 is as flowchart of the actions performed during an impedance imaging procedure, in accordance with some embodiments of the present invention. An electrical excitation signal at a suitable frequency is applied (70) to electrode 28. In an exemplary embodiment of the invention, the electrical excitation has a frequency of between about 0.1–5 MHz. Alternatively or additionally, higher or lower frequencies, for example of the order of a few kHz are used. Further alternatively or additionally, DC signals are used. In some embodiments of the invention, different frequencies are used for different procedures, i.e., detection of anomalies, location of anomalies and/or analysis of anomalies and/or for different body regions. Alternatively or additionally, an inspection procedure is repeated with a plurality of different frequencies, so as to provide more reliable results.

Each of sensing elements 22 senses (72) a series of measurements of the peak to peak amplitude of the currents which reach the element. In some embodiments of the invention, the sensed series of measurements includes a plurality of samples taken over a period which includes at least one cardiac cycle of the subject. The series of samples covers, in some embodiments, a plurality of cardiac cycles of the subject, within each of which cycles a plurality of samples are taken. In an exemplary embodiment of the invention, the sampling period is between about 5–10 seconds and includes between about 25–125 samples, equally or unequally distributed. In an exemplary embodiment of the invention, taking a single sample by a single sensing element 22 requires between about 10–100 microseconds, and samples are taken for substantially all of sensing elements 22 about every 0.1 seconds. Thus, in some embodiments, a single A/D converter 32 may service over 100 sensing elements 22.

Processing circuitry 34 receives the series of samples and determines (74) from the series of samples, a waveform of the changes in the samples. In some embodiments of the invention, the waveform of the changes in the samples is filtered (76) to remove changes which are due to noise (e.g., motion artifacts) and/or to extract signals which follow a separate signal of the subject (e.g., the cardiac cycle of the subject). In some embodiments of the invention, circuitry 34 determines (80) the amplitude of the filtered waveform of the changes (referred to in the following as the pulsatile amplitude) and displays (82) a surface map of region 39 which indicates (e.g., using colors, contours) the pulsatile amplitude of sensing elements 22. In a healthy breast 40, the surface map should conform to a predetermined distribution of the values of the pulsatile amplitude throughout region 39, which distribution is representative of healthy breasts. Certain anomalies, however, have significantly different blood volume than the surrounding healthy tissue of breast 40 and therefore will appear differently on the displayed map. In some embodiments of the invention, only areas which have abnormal pulsatile amplitude values, are displayed.

Alternatively or additionally to displaying a map of the pulsatile amplitude values, circuitry 34 performs an automatic comparison between the pulsatile amplitude values from different sensing elements 22 and accordingly provides locations of suspected anomalies, the depth of a suspected anomaly beneath surface 24 and/or a value indicative of the type of the anomaly.

In some embodiments of the invention, circuitry 34 compares the absolute determined pulsatile amplitude to predetermined known values for various types of tissues. The predetermined known values may depend on the distance between electrode 28 and probe 20 and/or on other measurement related parameters. In an embodiment of the invention, the distance between electrode 28 and probe 20 and/or the other measurement related parameters are entered (automatically or by a human operator based on measurements from separate apparatus) to circuitry 34, such that the circuitry selects the correct predetermined known values of the specific procedure.

Alternatively or additionally, circuitry 34 compares the difference between the pulsatile amplitude of a suspected anomaly and the pulsatile amplitude of surrounding tissue, to predetermined known values of pulsatile amplitude differences. For example, circuitry 34 may indicate areas in which there is a sharp difference (above a predetermined level) between the pulsatile amplitudes of adjacent sensing elements 22.

In some embodiments of the invention, the method of FIG. 2 is used to aid in anomaly detection, localization and/or analysis. Generally, cancerous anomalies have a larger blood volume than surrounding tissue, as cancerous anomalies generally include more blood vessels. Therefore, the changes during the cardiac cycle in the blood volume of a cancerous anomaly are larger than in normal tissue and the pulsatile amplitude is larger. Non-malignant anomalies, such as cysts, generally have a lower pulsatile amplitude than the surrounding tissue, due to their greater liquid content which does not include blood vessels. Thus, the use of the change waveform provides a better contrast between anomalies and their surrounding and/or between different types of anomalies, allowing detection and analysis of smaller anomalies than provided for by the art.

The area over which the pulsatile amplitude is influenced by the anomaly generally depends on the depth of the anomaly within breast 40. The area generally increases with the distance of the anomaly from probe 20. In addition, the pulsatile amplitude is generally a function of the depth and/or size of the anomaly. In some embodiments of the invention, after the depth and/or size of an anomaly are determined using any method described herein and/or otherwise known in the art, the pulsatile amplitude is normalized based on the depth and/or size of the anomaly so as to provide a value characteristic of the type (e.g., malignant or non-malignant) of the anomaly. Alternatively or additionally, the area over which the pulsatile amplitude is different from the surrounding tissue is normalized based on the depth and/or size of the anomaly and accordingly a value characteristic of the type of the anomaly is provided.

Referring in more detail to filtering (76) the determined waveform, in some embodiments of the invention, frequencies generally due to motion artifacts and other noise are removed from the determined waveform. In some embodiments of the invention, spectral analysis techniques are used in performing the filtering. Alternatively or additionally, band pass filtering is used around the frequency of the cardiac cycle in order to remove unrelated noise from the determined waveform. For example, the filtering may discard all the frequencies not in the band of 0.02–4 Hz. In some embodiments of the invention, frequencies characteristic of cyclic effects other than the cardiac cycle, e.g., the pulmonary and sympathetic effects, are removed from the determined waveform.

Alternatively, a waveform most closely characteristic of the cardiac cycle is extracted from the determined waveform. In an exemplary embodiment of the invention, the frequency of the cardiac cycle is determined from the sensed samples themselves. For example, circuitry 34 assumes that the frequency with the most distinct waveform is the frequency of the cardiac cycle and the waveform of this frequency is used in determining the pulsatile amplitude (80). Alternatively, the cardiac cycle frequency of the subject is determined (78), independent of the samples from probe 20, substantially concurrently with the sample taking of sensing elements 22, using any of the methods known in the art. These methods may include direct measurement of the pulse and/or indirect measurement of consequences of the pulse. In some embodiments of the invention, the frequency of the cardiac cycle is determined using plethysmography measurements on an organ of the subject, other than breast 40. In some embodiments of the invention, the plethysmography measurements are taken using electrical or light measurements as are known in the art. Alternatively or additionally, the frequency of the cardiac cycle is determined responsive to temperature changes of the subject's body surface. Further alternatively or additionally, the frequency of the cardiac cycle is determined responsive to variations in the magnetization of the subject's body.

In some embodiments of the invention, the filtering (76), is performed by searching for the extreme points of the sensed samples. In some embodiments of the invention, the extreme points are reviewed for their belonging to a desired waveform, e.g., a waveform which represents the cardiac cycle. Points not belonging to the desired waveform are weeded out. Alternatively or additionally, when no extreme points are included in the waveform for over a predetermined period, an extreme point is generated using suitable interpolation methods. In some embodiments of the invention, the reviewing of the extreme points includes fitting the extreme points to a plurality of pre-selected wavelets and choosing the wavelet which best fits the extreme points.

Alternatively or additionally, other processing methods may be used such as, for example, genetic algorithms, Markov models, neural networks and/or fuzzy logic.

In some embodiments of the invention, the reviewed extreme points are resampled into an even distribution in order to allow easy manipulation of the points in further processing, e.g., use of the fast frequency transform (FFT).

Alternatively or additionally to filtering (76) in order to determine the waveform of the cardiac cycle, other waveforms, cyclic or non-cyclic, which are indicative of physiological effects in the subject, are extracted from the determined (74) change waveform, using any of the methods described above. In some embodiments of the invention, the filtering (76) is performed in order to extract other cyclic waveforms, for example, waveforms due to the pulmonary and/or sympathetic effects. Alternatively or additionally, the filtering (76) is performed in order to extract a waveform which follows a related event, such as an internal and/or external stimuli. In some embodiments of the invention, the related event comprises an internal stimuli, such as a heart beat, for example in a subject with a non-regular cardiac cycle. In some embodiments of the invention, the external stimuli comprises pressure applied to the breast and/or a stimulate injected and/or otherwise applied to the subject.

In some embodiments of the invention, the filtering (76) includes relating to a portion of the waveform beginning a predetermined time (e.g., zero or longer) after the related event. Alternatively or additionally, the filtering (76) includes relating to a portion following an expected response to the event. For example, the filtering (76) may include relating to a portion of the waveform having a predetermined shape or other characteristic, for example a portion beginning with a large peak.

Alternatively or additionally, to determining (80) the pulsatile amplitude of the filtered change waveform, the frequency, duration, shape and/or any other parameter of the filtered change waveform are used in detecting, locating and/or analyzing anomalies. In some embodiments of the invention, the time delay from the related event until it causes a noticeable effect in the filtered change waveform. A fast propagation of the effect of the related event may indicate, for example, an anomaly having a large number of blood vessels. Optionally, the propagation time of the related event is determined for a plurality of points and is displayed as a map.

In some embodiments of the invention, a plurality of impedance imaging procedures such as described in FIG. 2 are performed with different stimulus. In an exemplary embodiment of the invention, a plurality of impedance imaging procedures are performed with different compression levels. Optionally, the breast is placed between a pair of compression plates which may apply different pressure levels to the breast. Impedance imaging procedures as described above are optionally performed with the plates applying different respective pressure levels to the breast.

In some embodiments of the invention, in addition to the pulsatile amplitude, other measurements from region 39 are used by processing circuitry 34 in generating indications on the existence, location and/or type of anomalies. In some embodiments of the invention, the other signal measurements from region 39 include additional information extracted from the signals sensed by probe 20, such as the value of the stationary portion of sensed samples (72). The processing of the stationary portion of the sensed samples, which is indicative of the impedance of a body portion beneath the sensor, may be performed, for example, as described in U.S. patent application Ser. No. 09/460,699, filed Dec. 14, 1999, the disclosure of which is incorporated herein by reference and/or in the above mentioned U.S. Pat.

No. 5,810,742. In some embodiments of the invention, a map of the pulsatile amplitudes is correlated with a map of the stationary portion of the sensed samples. In some embodiments, the map of the pulsatile amplitudes is overlaid on the map of the stationary portion of the sensed samples. Optionally, the overlaid map is displayed to a physician which searches for anomalies which have cancerous characteristics, i.e., an impedance indicative of cancerous flesh and a pulsatile amplitude indicative of high blood perfusion.

Alternatively or additionally, the other signal measurements include signals detected by apparatus other than probe 20, such as ultrasound and X-ray imaging apparatus and/or as described in PCT application PCT/IL00/00287, filed May 21, 2000, the disclosure of which is incorporated herein by reference.

In an exemplary embodiment of the invention, a breast checkup procedure comprises a plurality of stages. In a first stage, the breast is scanned using methods known in the art in order to determine whether there is a suspected anomaly within the breast. In a second stage, the precise location of the suspected anomaly is found, in particular the depth of the anomaly from surface 24. An exemplary method for determining the depth is performed using applied dipole electrical signals as described in the above mentioned U.S. patent application Ser. No. 09/460,699. Other methods, such as using x-ray and/or ultrasound imaging may also be used. In a third stage, electrification measurements are used to aid a physician in determining the type of the anomaly, i.e., whether the anomaly is cancerous or otherwise requires treatment, using the method described above with relation to FIG. 2, optionally with other measurements.

In some embodiments of the invention, electrode 28 is replaced by a long and narrow electrode which is placed substantially beneath a suspected anomaly. Using a long and narrow electrode reduces the dimensionality of the current reaching probe 20 directly from electrode 28. In some cases the direct current from electrode 28 may interfere with the detection of the current from an anomaly. These direct currents may be especially problematic when it is desired to extract the change waveform from the sensed signals. Alternatively or additionally, limited area electrodes of other shapes are used in applying signals to breast 40.

In some embodiments of the invention, the dimensionality of the applied signals is reduced even more by using applied signals which partially cancel each other, for example by electrifying two parallel long and narrow electrodes with opposite phases, for example, as is now described.

Figure 3A:
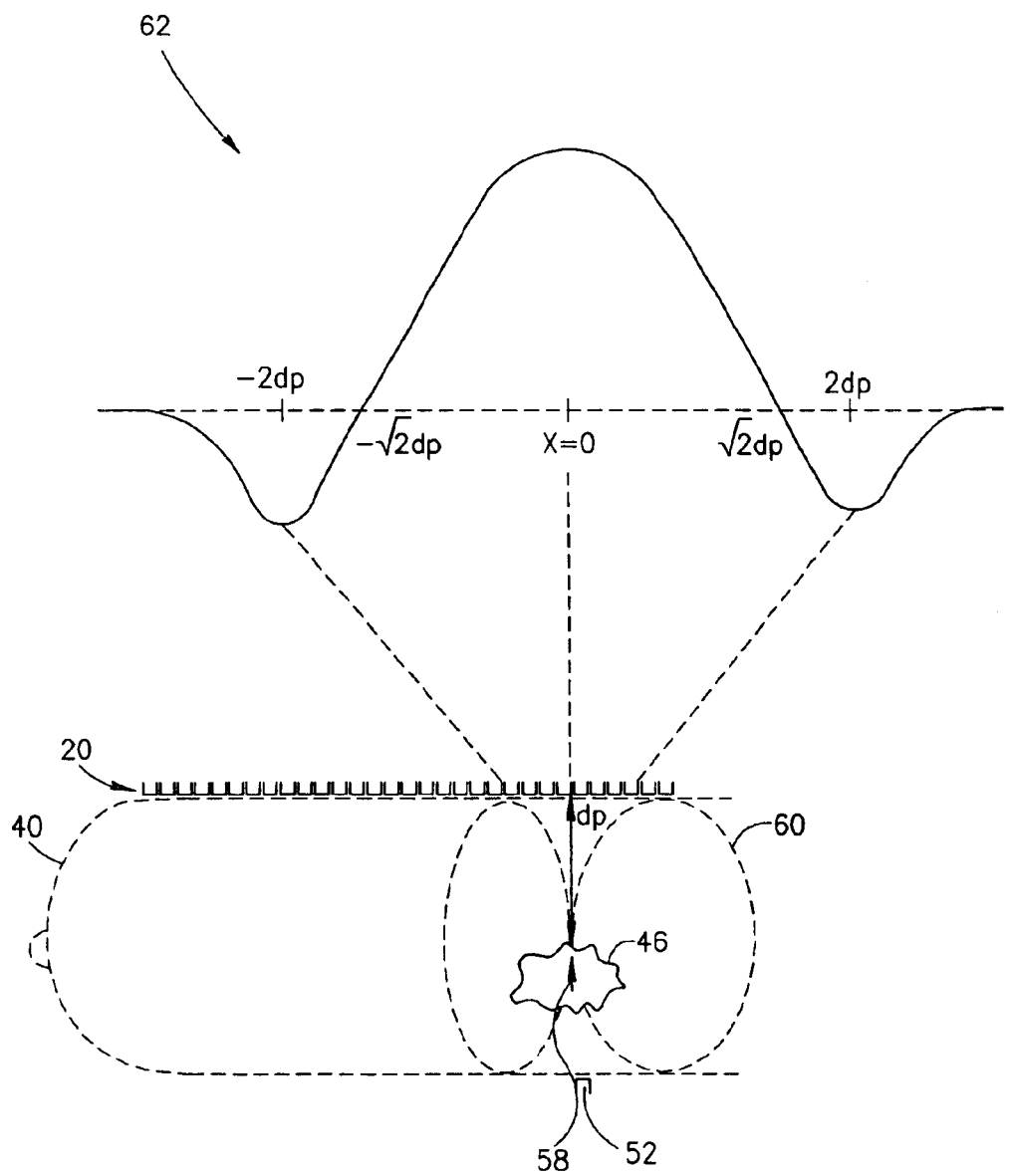
FIG. 3A is a schematic illustration of an anomaly evaluation procedure, in accordance with an embodiment of the present invention.

FIG. 3A is a schematic illustration of an impedance anomaly evaluation procedure, in accordance with an embodiment of the present invention. A probe 20 is placed on a surface of a breast 40 which includes an anomaly 46. Electrifying signals are applied to a long and narrow electrode 52, located substantially below anomaly 46. The electrification of electrode 52 induces a dipole, indicated by an arrow 58, within the anomaly. The dipole in anomaly 46 induces within breast 40 an electrical field indicated by dashed lines 60.

The influence of the dipole induced within anomaly 46 on sensing elements 22 is shown schematically by a graph 62. Graph 62 is a cross section of a normalized map formed by sensing elements 22, taken above anomaly 46. Blood volume changes in anomaly 46, due to the cardiac cycle, result in cyclic variations of the amplitude represented by graph 62. The waveform of these cyclic variations is determined from the samples, providing an indication of the type of anomaly 46. In some embodiments of the invention, the amplitude of the waveform of the cyclic variations is indicative of the blood volume of anomaly 46. The larger the blood volume of the anomaly, the larger the amplitude of the cyclic variations.

In some embodiments of the invention, the depth of anomaly 46 within breast 40 is determined, for example using methods described in U.S. patent application Ser. No. 09/460,699, and the amplitude of the cyclic variations is normalized accordingly. Alternatively or additionally, the size of the anomaly is determined, using any method known in the art, and accordingly the amplitude of the cyclic variations is normalized.

Figure 3B:
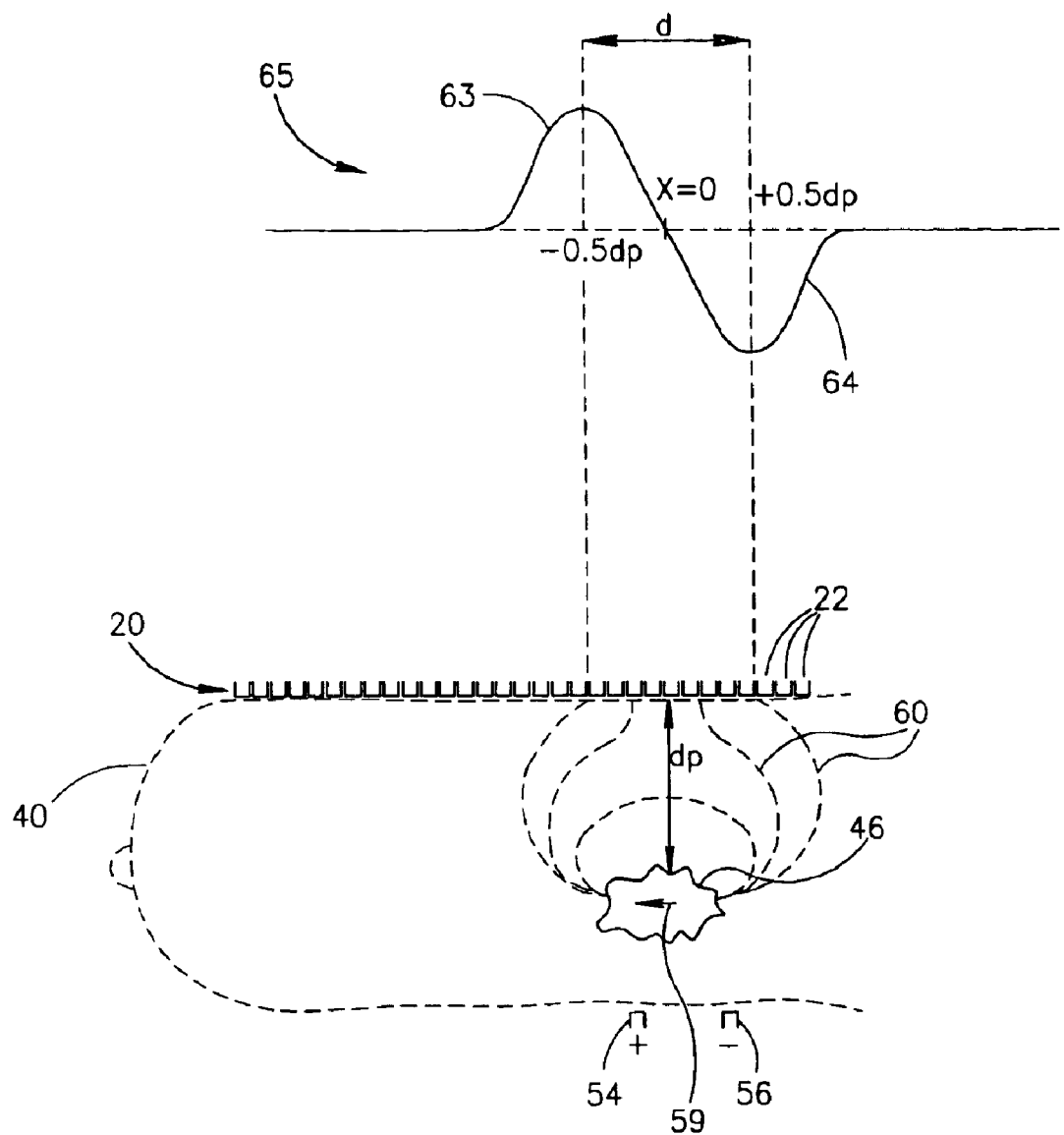
FIG. 3B is a schematic illustration of an anomaly evaluation procedure, in accordance with another embodiment of the present invention.

FIG. 3B is a schematic illustration of an impedance anomaly evaluation procedure, in accordance with an embodiment of the present invention. Electrification signals are applied to breast 40 from a pair of long and narrow electrodes 54 and 56, located on opposite sides of the projection of anomaly 46 on the surface of breast 40. In some embodiments of the present invention, electrifying signals of different phases, e.g., opposite polarities, are applied to electrodes 54 and 56. In an embodiment of the invention, the applied signals are adjusted such that they induce within anomaly 46 a dipole, indicated by an arrow 59, which is substantially parallel to probe 20. The influence of the dipole induced within anomaly 46 on sensing elements 22 is shown schematically by a graph 65. Graph 65 has two peaks 63 and 64 of substantially equal magnitude and opposite polarity. Blood volume changes in anomaly 46, due to the cardiac cycle, result in cyclic variations of the amplitude of graph 65. The waveform of these cyclic variations is determined from the samples, providing an indication of the type of anomaly 46.

The distance between peaks 63 and 64 is substantially equal to the depth of anomaly 46 beneath probe 20. In some embodiments of the invention, the depth of anomaly 46 is determined by measuring the distance between peaks 63 and 64. The determined depth of anomaly 46 is used to normalize any influence of the depth on the amplitude of the waveform of the changes of graph 65, such that the normalized graph is substantially only a function of the type of anomaly 46. Additional normalization procedures may be used, for example, as described in the above mentioned U.S. patent application Ser. No. 09/460,699.

It is noted that the current due to direct influence from electrodes 54 and 56 declines proportionally to the square of the distance and therefore interferes to a lesser extent in determining the current from anomaly 46 than current from a single electrode 52 as described above with reference to FIG. 3A.

In some embodiments of the invention, during a tissue characterization procedure the amplitude of the signals applied to electrode 54 and/or 56 is slowly changed until peaks 63 and 64 are of substantially equal magnitude. Alternatively or additionally, the applied signals are changed until the movements of graph 65 are most clearly determined.

Figure 4:
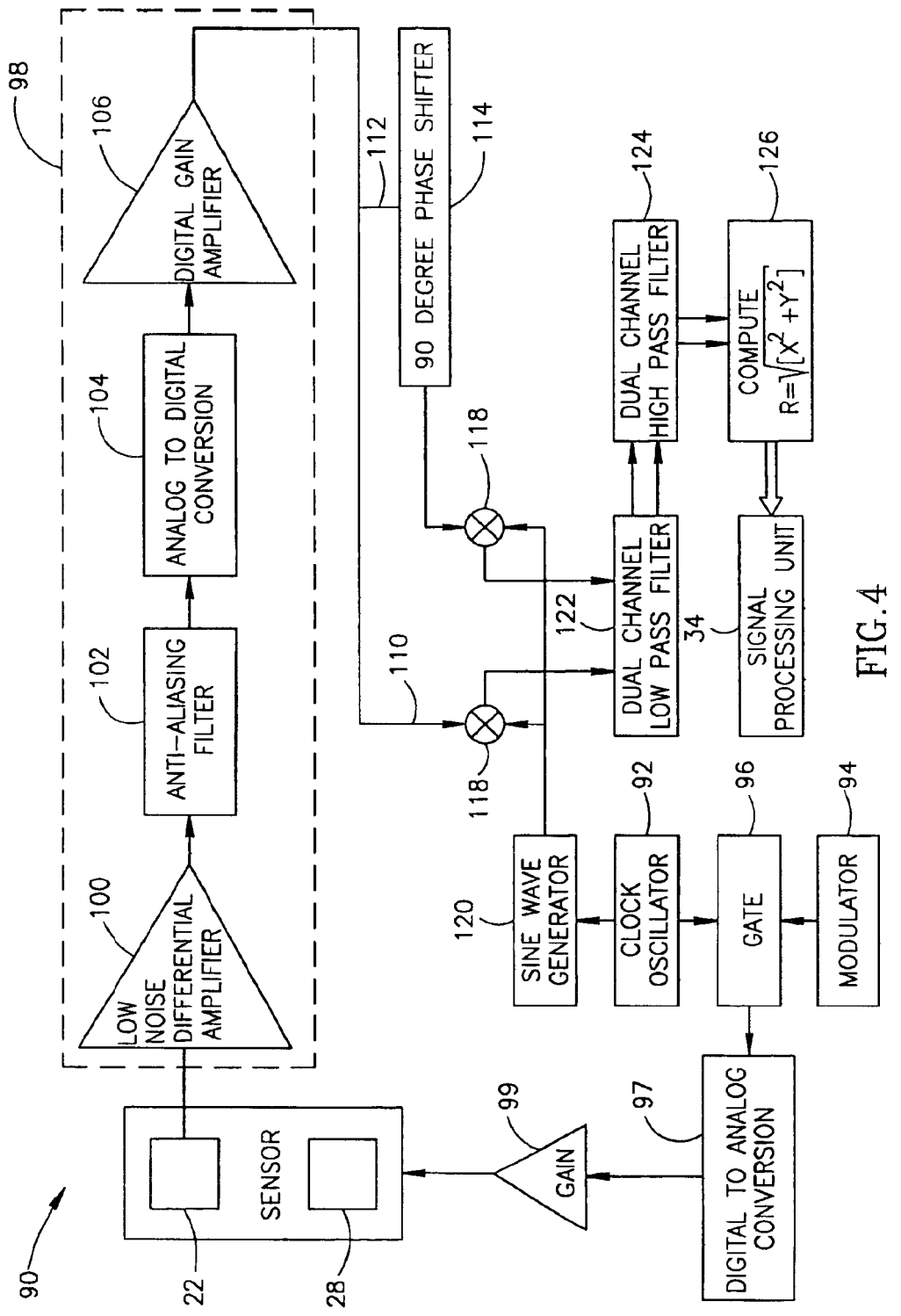
FIG. 4 is a schematic block diagram of apparatus for sensing currents for tissue characterization, in accordance with an embodiment of the present invention.

In some embodiments of the invention, a synchronous detection method, for example as described hereinbelow with reference to FIG. 4, is used to sense (72, FIG. 2) the samples by sensing elements 22. The use of synchronous detection reduces the affect of sporadic noise on the sampled signals. This reduction of the affect of the sporadic noise allows use of weaker excitation signals, use of lower resolution A/D converters and/or detection of weaker signals, i.e., higher detection resolution.

FIG. 4 is a schematic block diagram of apparatus 90 for sensing currents for impedance imaging and/or tissue characterization, in accordance with an embodiment of the present invention. In order to reduce the noise sensed by sensing element 22, the excitation signals applied to electrode 28 are provided in pulses. In some embodiments of the invention, a modulator 94 produces the excitation signal at a suitable frequency for impedance procedures. A clock oscillator 92 controls a gate 96 such that it passes the modulated signals to electrode 28 in pulses, for example, having a short duty cycle. In an embodiment of the invention, the signals are passed from gate 96 to electrode 28 via a D/A converter 97 and an amplifier 99, as is known in the art.

The signals sensed by sensing element 22 are amplified, filtered and digitized as is known in the art. The amplification, filtering and digitization may be performed, for example, in an acquisition path 98 which may include a low noise differential amplifier 100, an anti-aliasing filter 102, an analog to digital converter 104 and a digital amplifier 106. The signals from acquisition path 98 are directed over two separate lines 110 and 112. The signals on line 110 and/or line 112 are shifted such that the signals on lines 110 and 112 are shifted relative to each other by 90°. In an embodiment of the invention, the signals on line 112 are passed through a phase shifter 114 which shifts the signals by 90°. The signals on line 110 and those received from phase shifter 114 are multiplied, in respective multipliers 118, which serve as phase comparators, by a sine wave having the same period as the period of the pulses passed through gate 96. In some embodiments of the invention, the sine wave is generated by a wave generator 120 which is controlled by clock oscillator 92 which controls gate 96.

The multiplied signals from multipliers 118 are low passed filtered, e.g., by a dual channel low pass filter 122, in order to remove noise. In addition, the signals are filtered by a high pass filter 124 in order to reconstruct the signals from the pulse form they receive due to the pulse excitation. The signals are then combined using a combination unit 126. In some embodiments of the invention, combination unit 126 sums the squares of the signals on the lines and takes the square root of the sum. The combined signal is then processed to determine (74) the change waveform, as described hereinabove.

Alternatively to using two multipliers 118 and combination unit 126, a single multiplier 118 is used. The sine wave generator and/or a phase shifter of the signals from acquisition path 98 adjust the sine wave and/or the acquired signals such that they are phase aligned. A setting unit determines a required amount of phase shift of the sine wave and/or the acquired signals so that the sine wave and the acquired signals are aligned. It is noted, that the phase drift of the acquired signals is generally very slight and therefore the required amount of phase shift may be set once, e.g., upon power-on, or periodically at relatively large intervals.

The advantages in the use of the method of FIG. 2 and/or the apparatus of FIG. 4 is not limited to measurement of electrical currents using the apparatus of FIG. 1. Rather, in some embodiments of the invention the method of FIG. 2 and/or the apparatus of FIG. 4 are used with voltage measurements using the apparatus of FIG. 1 or other apparatus, such as four electrode setups. Furthermore, in some embodiments of the invention, the method of FIG. 2 and/or the apparatus of FIG. 4 are used to aid in detecting, locating and/or analyzing anomalies based on non-electrical signals. In some embodiments of the invention, excitation signals are applied using a near infrared LED and the detection is performed using one or more photo-diodes, e.g., a photo-diode array, such as a CCD. The LED and photo-diodes may be placed on opposite surfaces of an examined organ or may be aligned in any other manner known in the art.

In some embodiments of the invention, a probe is formed of two separable parts. A first part includes sensing apparatus, such as sensing elements 22, which depends on the type of signals (e.g., electrical, light) detected. Optionally, this part of the probe also includes an excitation source (e.g., electrode, LED). The second part includes acquisition and/or processing circuitry which is independent of the type of signals detected. Thus, a single acquisition and/or processing circuitry part may be used with a plurality of sensing and/or excitation parts.

In some embodiments of the invention, probe 20 or any other probe used for detecting, locating and/or analyzing anomalies in accordance with embodiments of the invention, comprises a battery operated, optionally hand held, probe. By providing the excitation to the body portion in pulses rather than in continuous excitation, the power consumption of the probe is reduced. In some embodiments of the invention, the sampling rate and hence the excitation pulse rate of the probe is chosen as a compromise between the accuracy achieved by a large number of samples, and the reduction of power consumption achieved by reducing the excitation pulse rate. Alternatively or additionally, the length of the sample sensing period is chosen as a compromise between accuracy and power consumption. It is noted that during long measurement periods the cardiac cycle may change and therefore very long sampling periods may not be advantageous for accuracy.

In some embodiments of the invention, before and/or during an anomaly detection, location and/or characterization procedure, materials which enhance the blood volume difference between an anomaly and surrounding tissue are injected to an inspected organ. Alternatively or additionally, materials which arise detectable biological signals, such as the sympathetic effect, are injected to the inspected organ. In some embodiments of the invention, the materials are injected generally to the inspected organ in the vicinity of the anomaly. Alternatively or additionally, the materials are injected directly into the anomaly, for example in a tissue characterization procedure. Exemplary materials include, for example, vasoconstriction and/or vasodilatation materials which are injected to the blood stream of the subject. Further alternatively or additionally, measures are taken to enhance the breathing rate of the subject, and thus enhance the changes in blood volume in suspected anomalies.

In some embodiments of the invention, before and/or during an inspection procedure, measures are taken in order to minimize irregularities in the subjects cardiac cycle. In some embodiments of the invention, a pulsatile regulation material, such as lidocain, is injected to the subject.

It is noted that although the present invention is not limited to detection, localization and/or analysis procedures of anomalies in the breast. Rather, the embodiments of the present invention may be used with many other human organs, for example, to aid in skin cancer detection, Cervical carcinoma detection and/or thyroid cancer detection. Furthermore, the embodiments of the invention may be used in tissue characterization in animals. It is further noted that the signal detection method described in relation to FIG. 4 may be used in detecting other low frequency biological signals.

It will be appreciated that the above described methods may be varied in many ways, including, changing the order of steps, and/or performing a plurality of steps concurrently. It should also be appreciated that the above described description of methods and apparatus are to be interpreted as including apparatus for carrying out the methods and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

What is claimed is:

1. A method of analyzing the type of tissue of a body portion of a subject, comprising:
    applying an excitation signal to the subject;
    sensing electrical signals from the subject responsive to the excitation signal;
    determining a stationary impedance map of the body portion responsive to the sensed signals;
    determining, for at least one pixel of the map, a waveform of a change over time in a parameter of the sensed electrical signals corresponding to the at least one pixel, which change waveform corresponds to a related event in the subject that is at least partially due to application of an external stimuli to the subject; and
    providing an indication on a tissue type of at least part of the body portion, responsive to the change waveform.

2. A method according to claim 1, comprising generating a change map which is a map of a parameter of the change waveform for the at least part of the stationary map.

3. A method according to claim 2, wherein generating the change map of a parameter of the change waveform comprises generating a change map of the amplitude of the change waveform.

4. A method according to claim 2, comprising displaying the change map.

5. A method according to claim 2, comprising correlating the change map and the stationary map.

6. A method according to claim 5, comprising displaying the change map overlaid on the stationary map.

7. A method according to claim 2, comprising determining areas of increased perfusion of blood in the body portion, responsive to the change map.

8. A method according to claim 1, wherein sensing the signals comprises sensing from a plurality of points on the surface of the body portion and determining the change waveform for each of the plurality of points.

9. A method according to claim 1, wherein sensing the signals comprises sensing electrical currents.

10. A method according to claim 1, wherein sensing the signals comprises sensing electrical voltages.

11. A method according to claim 1, wherein applying signals to the subject comprises applying electrification signals from at least two electrodes which are electrified with signals of different phases.

12. A method according to claim 1, wherein the application of the external stimuli to the subject comprises injecting a stimuli to the blood stream of the subject.

13. A method according to claim 1, wherein the application of the external stimuli to the subject comprises applying pressure to the body portion of the subject.

14. A method according to claim 1, wherein providing the indication comprises filtering at least one frequency from the change waveform and providing the indication responsive to the filtering waveform. analyzing the type of tissue of a body portion of a subject, comprising:
    applying an excitation signal to the subject;
    sensing signals from the subject responsive to the excitation signal;
    injecting a stimulus to the blood stream of the subject;
    extracting from the sensed signals a time dependent change waveform responsive to the injected stimulus; and
    providing an indication of whether the body portion includes cancerous tissue, responsive to the change waveform.

15. A method according to claim 1, wherein determining the time dependent change waveform comprises determining based on at least 25 samples taken at different times.

16. A method of analyzing the type of tissue of a body portion of a subject, comprising:
    applying an excitation signal to the subject;
    sensing signals from the subject responsive to the excitation signal;
    injecting a stimulus to the blood stream of the subject;
    extracting from the sensed signals a time dependent change waveform of a change in a parameter of the sensed signals, responsive to the injected stimulus; and
    providing an indication of an identification of a tissue type of at least part of the body portion, responsive to the change waveform,
    wherein sensing the signals comprises sensing signals at a plurality of points on the surface of the body portion and determining the change waveform for each of the plurality of points.

17. A method according to claim 16, comprising determining the amplitude of the chage waveform.

18. A method according to claim 16, wherein sensing signals from the subject comprises sensing electrical signals.

19. A method according to claim 16, wherein providing the indication comprises filtering at least one frequency from the change waveform and providing the indication responsive to the filtered waveform.

20. A method according to claim 16, wherein determining the time dependent change waveform comprises determining based on at least 3 samples taken at different times.

21. A method according to claim 16, wherein determining the time dependent change waveform comprises determining based on at least 25 samples taken at different times.

22. A method according to claim 16, wherein determining the time dependent change waveform comprises determining based on samples acquired in a plurality of cardiac cycles of the patient, a plurality of samples being acquired in each cardiac cycle.

23. A method of analyzing the type of tissue of a body portion of a subject, comprising:

applying an excitation signal to the subject;

sensing signals from the subject responsive to the excitation signal;

injecting a stimulus to the blood stream of the subject;

extracting from the sensed signals a time dependent change waveform of a change in a parameter of the sensed signals, responsive to the change waveform, wherein sensing the signals comprises sensing signals at a plurality of points on the surface of the body portion and determining the change waveform for each of the plurality of points.

24. A method according to claim 23, wherein providing the indication on tissue type of at least part of the body portion comprises providing indication on whether an anomaly is malignant.

25. A method according to claim 23, wherein providing the indication comprises filtering at least one freqeuncy from the change waveform and provdiding the indication responsive to the filtered waveform.

26. A method according to claim 23, wherein determining the time dependent change waveform comprises determining based on at least 25 samples taken at different times.

27. A method of analyzing the type of tissue of a body portion of a subject, comprising:

applying an excitation signal to the subject;

sensing signals from the subject responsive to the excitation signal;

injecting a stimulus to the blood stream of the subject;

extracting from the sensed signals a response to the injected stimulus; and generating a map, including for each pixel a parameter value characterizing the response to the injected stimulus at a corresponding location of the body portion.

28. A method according to claim 27, wherein sensing signals from the subject comprises sensing electrical signals.

29. A method according to claim 27, wherein generating the map comprises generating a map in which each pixel has a value of a pulsatile amplitude.

30. A method according to claim 27, comprising determining whether the subject has cancer responsive to the map.

31. A method according to claim 27, comprising determining whether the subject has cancer responsive to the map.

32. A method according to claim 27, wherein extracting the response from the sensed signals comprises extracting at least one frequency from the sensed signals.

33. A method according to claim 27, wherein extracting the response from the sensed signals comprises extracting a response based on at least 3 samples taken at different times.

34. A method according to claim 27, wherein extracting the response from the sensed signals comprises extracting a response based on at least 25 samples taken at different times.

35. A method according to claim 27, wherein extracting the response from the sensed signals comprises extracting a response based on a plurality of samples acquired in each of a plurality of cardiac cycles of the patient.

* * * * *